(12) United States Patent
Williams et al.

(10) Patent No.: US 7,359,804 B2
(45) Date of Patent: Apr. 15, 2008

(54) SYSTEM AND METHOD FOR CALIBRATING REMOTE EMISSIONS SENSING INSTRUMENTS

(75) Inventors: Mitchell Jared Williams, Denver, CO (US); Donald H. Stedman, Denver, CO (US)

(73) Assignee: Environmental Systems Products Holdings Inc., East Granby, CT (US)

( * ) Notice: Subject to any disclaimer, the term of this patent is extended or adjusted under 35 U.S.C. 154(b) by 112 days.

(21) Appl. No.: 11/210,765

(22) Filed: Aug. 25, 2005

(65) Prior Publication Data

US 2006/0047445 A1 Mar. 2, 2006

Related U.S. Application Data

(60) Provisional application No. 60/604,011, filed on Aug. 25, 2004.

(51) Int. Cl.
*G06F 19/00* (2006.01)
*G01N 21/17* (2006.01)

(52) U.S. Cl. .............. 702/28; 73/1.01; 73/1.02; 73/1.03; 73/1.06; 73/1.07; 73/23.2; 73/23.21; 73/23.22; 73/23.35; 73/23.36; 436/43; 702/22; 702/23; 702/27; 702/30

(58) Field of Classification Search ............ 73/1.01, 73/1.02, 1.03, 1.06, 1.07, 23.2, 23.21, 23.22, 73/23.31, 23.32, 23.33, 23.35, 23.36, 23.37, 73/23.38; 436/43; 702/22, 23, 24, 27, 28, 702/30
See application file for complete search history.

(56) References Cited

U.S. PATENT DOCUMENTS

| | | | | |
|---|---|---|---|---|
| 2,995,410 A | * | 8/1961 | McDonell et al. ............ 346/23 |
| 3,177,138 A | * | 4/1965 | Larrison ................ 208/351 |
| 3,359,784 A | * | 12/1967 | Jorre et al. ............. 73/23.2 |
| 3,547,541 A | * | 12/1970 | Varnela ................ 356/306 |
| 3,556,950 A | * | 1/1971 | Dahms ................. 205/775 |
| 3,957,372 A | * | 5/1976 | Jowett et al. ............ 356/51 |
| 3,958,122 A | * | 5/1976 | Jowett et al. ........... 250/346 |
| 3,973,848 A | * | 8/1976 | Jowett et al. ............ 356/51 |
| 4,750,139 A | | 6/1988 | Dils | |
| 5,060,505 A | * | 10/1991 | Tury et al. ............. 250/343 |

(Continued)

FOREIGN PATENT DOCUMENTS

CA 2131865 * 3/1995

(Continued)

OTHER PUBLICATIONS

Bishop, Gary A., et al., "IR Long-Path Photometry: A Remote Sensing Tool for Automobile Emissions," 1989; reprinted from *Analytical Chemistry*, vol. 61, No. 10, May 15, 1989, pp. 671A-676A.

(Continued)

*Primary Examiner*—Edward R Cosimano
(74) *Attorney, Agent, or Firm*—Pillsbury Winthrop Shaw Pittman, LLP

(57) ABSTRACT

A system and method is provided for obtaining calibration curves for CO and $CO_2$ during laboratory calibration of one or more remote emissions sensing (RES) instruments, and for self-calibration of on-road RES instruments to compensate for changes in background CO and $CO_2$ column densities.

14 Claims, 8 Drawing Sheets

U.S. PATENT DOCUMENTS

| | | | | |
|---|---|---|---|---|
| 5,210,702 | A | * | 5/1993 | Bishop et al. ................. 702/24 |
| 5,210,778 | A | * | 5/1993 | Massart ........................ 378/53 |
| 5,315,528 | A | * | 5/1994 | L'vov .......................... 702/23 |
| 5,319,199 | A | * | 6/1994 | Stedman et al. .......... 250/338.5 |
| 5,334,536 | A | * | 8/1994 | Nonnenmacher ........... 436/135 |
| 5,343,043 | A |   | 8/1994 | Johnson |
| 5,371,367 | A |   | 12/1994 | DiDomenico et al. |
| 5,401,967 | A | * | 3/1995 | Stedman et al. .......... 250/338.5 |
| 5,418,366 | A |   | 5/1995 | Rubin et al. |
| 5,489,777 | A |   | 2/1996 | Stedman et al. |
| 5,498,872 | A | * | 3/1996 | Stedman et al. .......... 250/338.5 |
| 5,552,997 | A | * | 9/1996 | Massart ........................ 702/85 |
| 5,591,975 | A | * | 1/1997 | Jack et al. ................ 250/338.5 |
| 5,644,133 | A |   | 7/1997 | Didomenico et al. |
| 5,719,396 | A |   | 2/1998 | Jack et al. |
| 5,726,450 | A | * | 3/1998 | Peterson et al. .......... 250/338.5 |
| 5,739,413 | A |   | 4/1998 | Kohn et al. |
| 5,797,682 | A | * | 8/1998 | Kert et al. ................... 374/123 |
| 5,831,267 | A | * | 11/1998 | Jack et al. ................ 250/338.5 |
| 6,107,631 | A | * | 8/2000 | He ......................... 250/339.09 |
| 6,307,201 | B1 |   | 10/2001 | Didomenico et al. |
| 6,375,828 | B2 |   | 4/2002 | Ando et al. |
| 6,396,056 | B1 |   | 5/2002 | Lord et al. |
| 6,455,851 | B1 | * | 9/2002 | Lord et al. ............... 250/338.5 |
| 6,560,545 | B2 |   | 5/2003 | Stedman et al. |
| 6,670,613 | B2 | * | 12/2003 | Prozzo et al. ............... 250/345 |
| 6,671,630 | B2 |   | 12/2003 | Stedman et al. |
| 6,723,989 | B1 |   | 4/2004 | Didomenico et al. |
| 6,983,639 | B1 |   | 1/2006 | DiDomenico et al. |
| 7,192,782 | B2 | * | 3/2007 | Roller et al. ................ 436/116 |
| 2001/0045521 | A1 | * | 11/2001 | Prozzo et al. ............... 250/345 |
| 2002/0052698 | A1 |   | 5/2002 | Didomenico et al. |
| 2002/0130053 | A1 |   | 9/2002 | Ando et al. |
| 2003/0089854 | A1 |   | 5/2003 | Shifflett et al. |
| 2003/0120434 | A1 |   | 6/2003 | DiDomenico et al. |
| 2003/0134427 | A1 | * | 7/2003 | Roller et al. ................ 436/171 |
| 2004/0155191 | A1 |   | 8/2004 | Stedman et al. |
| 2006/0047445 | A1 | * | 3/2006 | Williams et al. .............. 702/30 |
| 2007/0081162 | A1 | * | 4/2007 | Roller et al. ................ 356/437 |

FOREIGN PATENT DOCUMENTS

| | | | |
|---|---|---|---|
| EP | 0 414 446 A2 | * | 2/1991 |
| EP | 0 417 884 A2 | * | 3/1991 |
| EP | 0 453 036 A2 | * | 10/1991 |
| EP | 0 681 179 A1 | * | 11/1995 |
| WO | WO 92/12411 |   | 7/1992 |
| WO | WO 98/37405 |   | 8/1998 |
| WO | WO 99/46578 A1 | * | 9/1999 |
| WO | WO 02/082059 |   | 10/2002 |

OTHER PUBLICATIONS

Bishop, Gary A., et al., "Oxygenated Fuels, A Remote Sensing Evaluation", *SAE Technical Paper Series*; Copyright 1989, Society of Automotive Engineers, Inc.; pp. 1-8.

"An Analysis of On-Road Remote Sensing as a Tool for Automobile Emissions Control," Final Report Prepared by University of Denver Chemistry Department, Colorado, prepared for Illinois Department of Energy and Natural Resources, Mar. 1990, 174 pages.

Stedman, Donald H., et al., "Remote Sensing of On-Road Vehicle Emissions," Contract No. VE-8-1, Final Report to Coordinating Research Council, The University of Denver, Jan. 6, 1992, 21 pages.

Bishop, Gary A., et al., "Enhancements of Remote Sensing for Vehicle Emissions in Tunnels," *Air & Waste Management Association*, vol. 44, Feb. 1994, pp. 169-175.

Guenther, Paul Leonard, "Contributions to On-Road Remote Sensing of Automobile Exhaust," A Thesis Presented to the Faculty of Natural Sciences, Mathematics, and Engineering, University of Denver, Jun. 1992, 95 pages.

Stedman, Donald H., et al., "On-Road Remote Sensing of CO and HC Emissions in California", Prepared for Research Division, California Air Resources Board, Sacramento, California, submitted by University of Denver Chemistry Department, Feb. 1994, 136 pages.

RSD 1000 Operator's Manual (Preliminary), Remote Sensing Technologies, IFB No. 94019, Jun. 1993, 66 pages.

Stedman, Donald H., "Automobile Carbon Monoxide Emission", *Environmental Science & Technology*, vol. 23, No. 2, 1989, pp. 147-149.

Stedman, Donald H., et al., "Evaluation of a Remote Sensor for Mobile Source CO Emissions", U.S. Environmental Protection Agency, CR-815778-01-0, Report No. EPA/600/4-90/032, Jan. 1991, 90 pages.

Bishop, Gary A., et al., "Infrared Emission and Remote Sensing", *Journal of the Air & Waste Management Association*, vol. 42, No. 5, May 1992, pp. 695-697.

Bishop, Gary A., et al., "Method Comparisons of Vehicle Emissions Measurements in the Fort McHenry and Tuscarora Mountain Tunnels", *Atmospheric Environment*, vol. 30, No. 12, 1996, pp. 2307-2316.

Stedman, Donald H., et al., "NOx Data by Remote Sensing", Published by the Coordinating Research Council, Published for the 5$^{th}$ CRC On-Road Vehicle Emissions Workshop, Apr. 3-5, 1995, 16 pages.

Stedman, Donald H., et al., "On-Road Carbon Monoxide and Hydrocarbon Remote Sensing in the Chicago Area", Final Report Prepared by University of Denver Chemistry Department, Prepared for Illinois Department of Energy and Natural Resources, Office of Research and Planning, Illinois Contract AQ 40, Project 91/122, Report No. ILENR/RE-AQ-91/14, Oct. 1991, pp. 1-70.

Bishop, Gary A., et al., "On-Road Carbon Monoxide Emission Measurement Comparisons for the 1988-1989 Colorado Oxy-Fuels Program", *Environmental Science & Technology*, vol. 24, No. 6, 1990, pp. 843-847.

Stedman, Donald H., et al., "On-Road CO Remote Sensing in the Los Angeles Basin", Final Report Prepared for the Research Division, California Air Resources Board, Submitted by University of Denver Chemistry Department, Aug. 1991, Contract No. A932-189, 70 pages.

Bishop, Gary A., et al., "Analytical Approach—IR Long-Path Photometry: A Remote Sensing Tool for Automotive Emissions", *Analytical Chemistry*, vol. 61, No. 10, May 15, 1989, pp. 671A-677A.

Stedman, Donald H., "Science and Politics of Air Pollution From Cars," Mar. 1995, pp. 1-11.

Stedman, Donald H., "An Analysis of On-Road Remote Sensing as a Tool for Automobile Emissions Control", Illinois Dept. of Energy and Natural Resources, Mar. 1990, ILENR/RE-AQ-90/05.

Stedman, Donald, et al., "On-Road CO, HC, NO and Opacity Measurements", 7$^{th}$ *CRC On-Road Vehicle Emissions Workshop*, Apr. 9-11, 1997, pp. 8-25 and 8-27 to 8-33.

RSD 3000 Operator's Manual, Remote Sensing Technologies, Inc., Apr. 21, 1998, pp. 1-49.

"Data Processing Manual", Remote Sensing Technologies, Inc., Feb. 10, 1998, pp. 27.

Williams, Mitchell Jared, "Advances in On-Road Remote Sensing [Microform]: Feat 5000 The Next Generation", Thesis, University of Denver, MAS 2003 No. 27, Aug. 2003, 147 pages.

* cited by examiner

SYSTEM AND METHOD FOR CALIBRATING REMOTE EMISSIONS SENSING INSTRUMENTS

CROSS-REFERENCE TO RELATED APPLICATIONS

This Application claims priority from U.S. Provisional Patent Application Ser. No. 60/604,011, filed Aug. 25, 2004 (now expired), which is incorporated herein by reference in its entirety.

FIELD OF THE INVENTION

The invention relates generally to remote emissions sensing (RES) systems and methods, and more particularly to a system and method for obtaining calibration curves for CO, $CO_2$, and other gases during laboratory calibration of one or more RES instruments, and for self-calibration of on-road RES instruments to compensate for changes in background CO and $CO_2$ concentrations.

BACKGROUND OF THE INVENTION

Remote emissions sensing (RES) systems are known. Such systems are generally utilized for remotely monitoring the exhaust gas composition of motor vehicles. Examples of RES systems and methods are described in, for example, U.S. Pat. Nos. 5,210,702, 5,319,199, 5,401,967, 5,591,975, 5,726,450, 5,797,682, and 5,831,267, each of which is hereby incorporated herein by reference in its entirety.

Despite steady advances in their sophistication and robustness, the manufacture and/or calibration of some instruments (e.g., detectors or detector arrays) utilized in RES systems may suffer from various drawbacks. For instance, one drawback associated with instrument manufacture is the need to separately calibrate each detector channel with known column densities of relevant pollutant gases.

Additionally, when remotely monitoring the exhaust gas composition of motor vehicles on a roadway or driving surface under various operating conditions, it may be expensive and/or inconvenient to have to repeatedly recalibrate on-road instruments using expensive, certified gas cylinders of surrogate exhaust pollutants. Such recalibration may be necessary for conventional instruments to compensate for changes in background (or ambient) CO and $CO_2$ concentrations over time. $CO_2$, for example, is reasonably abundant in the atmospheric optical path used for measurement, and may vary with wind speed, wind direction, and traffic volume, among other factors. These and other drawbacks exist with known calibration methods.

SUMMARY OF THE INVENTION

The invention solving these and other problems relates to a system and method for obtaining calibration curves for CO, $CO_2$, and other gases during laboratory calibration of one or more RES instruments, and for self-calibration of on-road RES instruments to compensate for changes in background CO and $CO_2$ concentrations.

As used herein, a RES system may comprise any components present when remotely monitoring the exhaust gas composition of motor vehicles on a roadway or driving surface at a given test site (or in the "field"), under various operating conditions. Examples of such components may include, but are not limited to, a source, detector (or detector array), transfer optics, certified gas cylinder, imaging unit, speed and acceleration detection unit, thermal detection unit, processor, communicator, or other components. Additionally, one or more RES components may be referred to herein interchangeably as RES instruments. Moreover, as used herein, an optical absorption-based multi-gas analyzer (OABMGA) may comprise one or more RES components (or instruments) including, for example, a source, detector (or detector array), transfer optics, processor, or other components.

One aspect of the invention relates to obtaining calibration curves for CO, $CO_2$, and other gases during laboratory calibration of one or more RES instruments. In one embodiment, a linear absorption curve may be generated for at least one gas in a laboratory setting. In one implementation, for example, gas cell calibration for an HC detector channel may be performed by inserting a gas cell having a known concentration of propane into an optical measurement path. Propane may be used as the surrogate HC. In a laboratory setting, it may reasonably be assumed that the ambient concentration of propane is zero. The HC gas cell calibration results in a linear correlation between absorption and HC column density.

Once the linear correlation between absorption and HC column density has been obtained via HC gas cell calibration, one or more RES components (e.g., source and detector) may be isolated from outside (or ambient) air in the laboratory setting to accomplish a single gas pulse (or puff) calibration. In particular, a known gas mixture of CO, $CO_2$, HC, $N_2$, or other gases may be injected into the optical measurement path from a gas cylinder and raw voltage data for each gas may be acquired from a corresponding detector channel.

The linear absorption curve correlating absorption and HC column density may be used in conjunction with the time-variable puff of gas from the cylinder containing a plurality of gases at known concentration ratios to derive calibration curves for CO, $CO_2$, and other gases, as described in detail herein. In this manner, the need to separately calibrate each detector channel with known column densities of relevant pollutant gases may be avoided.

An additional aspect of the invention relates to self-calibration of on-road RES instruments to compensate for changes in background CO and $CO_2$ concentrations. According to an embodiment of the invention, to be "self-calibrating," RES instruments may be adapted to continuously monitor the changes in background (or ambient) concentrations of those pollutants which have non-linear, background-dependent calibration curves, so as to remain correctly calibrated.

In particular, the system and method may utilize a combination of signals from detector channels which respond to the pollutants in question and detector channels which provide reference signals. The detector channels may be provided by either a plurality of detectors with different optical filters, or a single detector observing through a plurality of optical filters. In one implementation, the optical filters may include gas cells as in the method known as gas filter correlation spectroscopy. In one embodiment, a first detector channel may monitor $CO_2$ at an IR wavelength of approximately 4.3 micron absorption, and a reference channel may monitor an IR wavelength of approximately 3.9 microns at which no gas absorption is expected. With this capability, a RES instrument may be calibrated once in the laboratory (as described above), and then used to obtain correct readings at virtually any location in the field without recalibration.

According to one implementation, local background pollutant concentrations at a vehicle emissions test site may be determined using a gas puff from a calibration cylinder, or the insertion of a gas cell with known pollutant concentrations. In this regard, any individual channel gain changes which might have taken place since the laboratory calibration may be accounted (or corrected) for. Background levels may be continuously updated based upon voltage signals collected in front of passing motor vehicles whose emissions are to be quantitatively detected. Pollutant background changes as a function of time may be evaluated to identify both slow and fast changes, and the software accepting vehicle emissions readings may be adjusted depending upon how stable the background concentrations are measured to be. In this manner, the expensive and/or inconvenience associated with having to repeatedly recalibrate on-road instruments using expensive, certified gas cylinders of surrogate exhaust pollutants may be avoided.

The various objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION OF PREFERRED EMBODIMENTS

An aspect of the invention relating to obtaining calibration curves for CO, $CO_2$, and other gases during laboratory calibration of one or more RES instruments will first be described. A description of an exemplary RES system for remotely monitoring the exhaust gas composition of motor vehicles on a roadway or driving surface at a given test site (or in the "field"), under various operating conditions will then be provided, followed by a detailed description of the self-calibration of on-road RES instruments to compensate for changes in background CO and $CO_2$ concentrations.

I. Laboratory Calibration

Figure 1A:
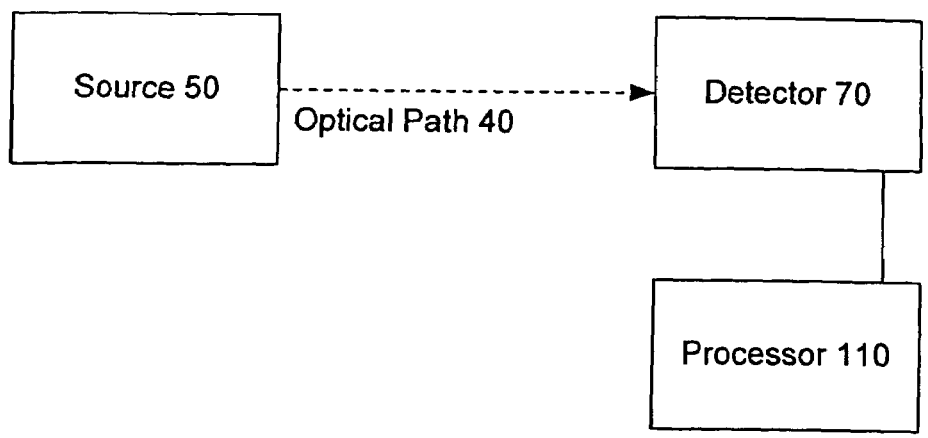
FIG. 1A is an exemplary illustration of an optical absorption-based multi-gas analyzer (OABMGA) in a laboratory environment, according to an embodiment of the invention.

According to an embodiment of the invention illustrated in FIG. 1A, an optical absorption-based multi-gas analyzer (OABMGA) 100 is provided in a laboratory environment comprising a source 50, one or more detectors or a detector array 70, and processor 110. In various implementations, as described in detail below, additional components may be provided.

Source 50 may comprise one or more sources of electromagnetic radiation (ER) which may be used in the absorption spectroscopy measurement of various gases in an optical path 40 (including, for example, components of vehicle exhaust emissions) in a known manner. Source 50 may comprise an infrared (IR) radiation source. In alternative embodiments, other types of radiation sources may be used including, for example, an ultraviolet (UV) source, a visible light source, or other suitable sources as known and understood by those having skill in the art. In some embodiments, a combination of radiation sources may be used.

Detector array 70 is preferably chosen to permit detection of electromagnetic radiation emitted by source 50. For example, detector array 70 may comprise a photodetector (e.g., a photodiode), a photomultiplier tube (PMT), a spectrometer, or any other suitable radiation detector. A mercury cadmium telluride (Hg—Cd—Te) or lead selenide photodetector may also be used to detect IR radiation. Other suitable detectors or detector arrays or combinations thereof may also be used. For instance, in some implementations, a single detector with multiple filters may be utilized instead of an array employing multiple detectors. The multiple filters may be moveable, such as spinning filters, to allow multiple components of a gas sample (e.g., vehicle exhaust components) in optical path 40 to be detected. In this regard, a single detector can be employed to detect a plurality of different components because each of the moveable filters is designed to allow only the wavelength band of interest by a particular component to pass to the detector.

According to an embodiment of the invention, processor 110 may comprise a suitable processing device such as, for example, a computer or other microprocessor. Processor 110 may optionally employ software to accomplish desired analysis of collected and/or stored data in a known manner (subject to the improvements described herein). For example, with regard to a gas sample present in optical path 40, software may be used to calculate the relative amounts of various constituents of the gas sample, concentrations of various constituents of the gas sample (e.g., HC, $CO_2$, $NO_x$, CO, etc.), and the decay rate (e.g., dissipation in time) of the constituents, among other things. Processor 110 may further comprise or interface to a graphical user interface (GUI) for enabling a user to access, navigate, and otherwise utilize the various software processing functions described herein.

According to an embodiment of the invention, source 50 may be configured to pass a beam of EM radiation through a gas sample in optical path 40. Detector array 70 may be configured to receive the beam after it passes through the gas sample. One or more filters (not illustrated) may be associated with detector array 70 to enable detector array 70 to determine the intensity of EM radiation having a particular wavelength or range of wavelengths. The wavelengths may be selected to correspond to wavelengths absorbed by molecular species of interest in the gas sample (e.g., hydrocarbons (HC), carbon monoxide (CO), carbon dioxide ($CO_2$) and nitrogen oxides ($NO_x$) such as NO and $NO_2$). One or more detector output voltages represent the intensity of the EM radiation measured by that detector. Detector array 70 may be configured such that each molecular species of interest in the gas sample has a unique detector channel.

The detector output voltages may then be input to processor 110. Processor 110 may calculate the difference between the known intensity of source 50 and the intensity detected by the detectors to determine the amount of absorption by the particular molecular species (based on predetermined wavelengths associated with that species). Based on the measured absorption(s), the column density of one or more molecular species in the gas sample may be determined in a known manner.

As recited above, one of the less satisfactory aspects of RES instrument manufacture is the need to separately calibrate each detector channel with known column densities of relevant pollutant gases. According to an embodiment of the invention, a system and method for overcoming this drawback is provided, wherein at least one hydrocarbon detector channel is carefully calibrated with propane (or other suitable gas), and the resulting linear calibration curve is used to establish calibration equations for a predetermined number of other detector channels via a single pulse (or puff) of gas with a certified mixture of known concentrations. Alternate configurations (e.g., one or more puffs for varying predetermined time periods) may be utilized.

According to an embodiment of the invention, for calibration, a predetermined linear absorption curve may be generated for at least one gas. For example, in one implementation, gas cell calibration for an HC detector channel may be performed by inserting a gas cell (not illustrated) having a known concentration of propane (or other suitable gas), into optical path 40. Propane may be used as the surrogate HC. Gas-cell calibration for an HC detector channel may be performed with greater reliability as it can be reasonably assumed that, in a laboratory setting, the ambient concentration of propane is zero.

Figure 2:
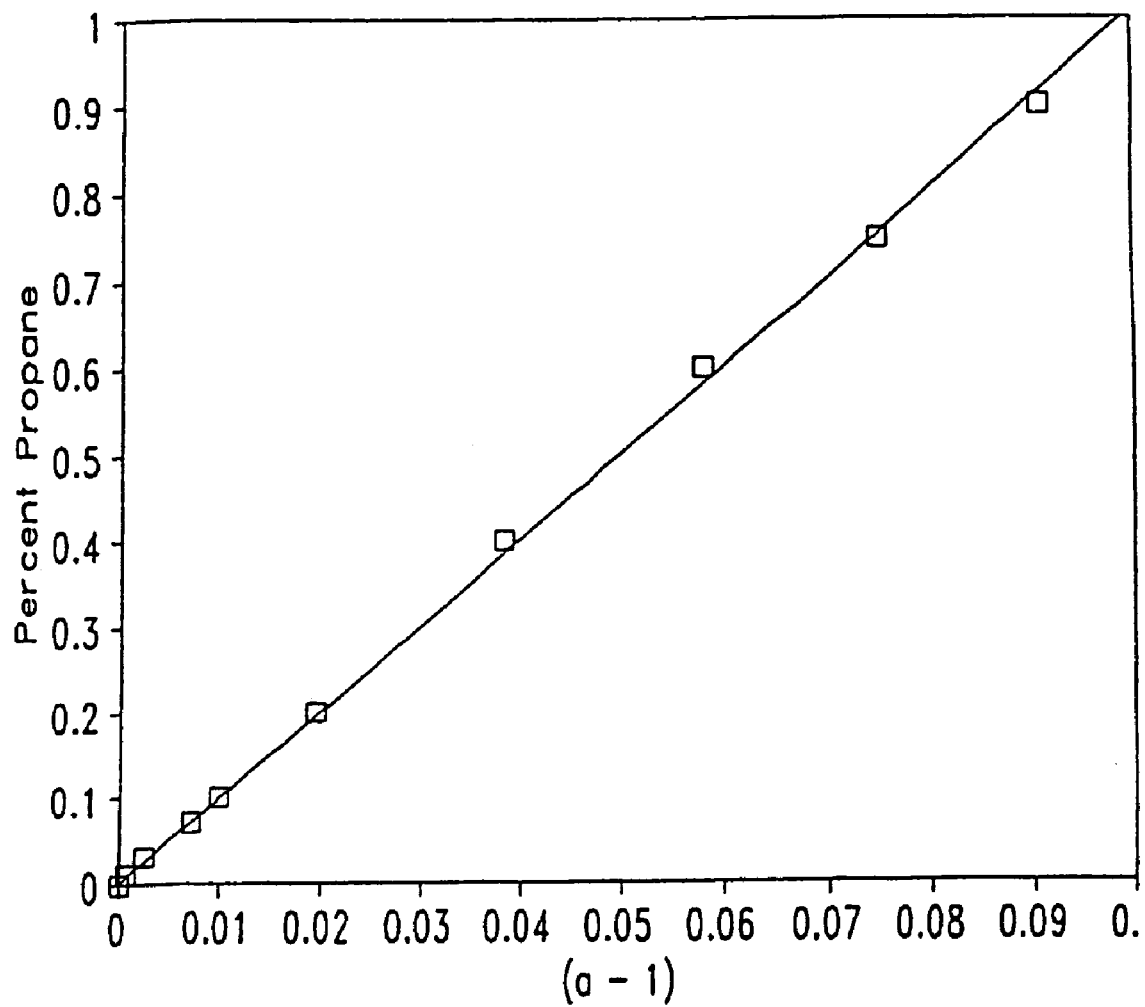
FIG. 2 depicts a calibration curve illustrating the linear calibration of an HC channel.
Figure 3:
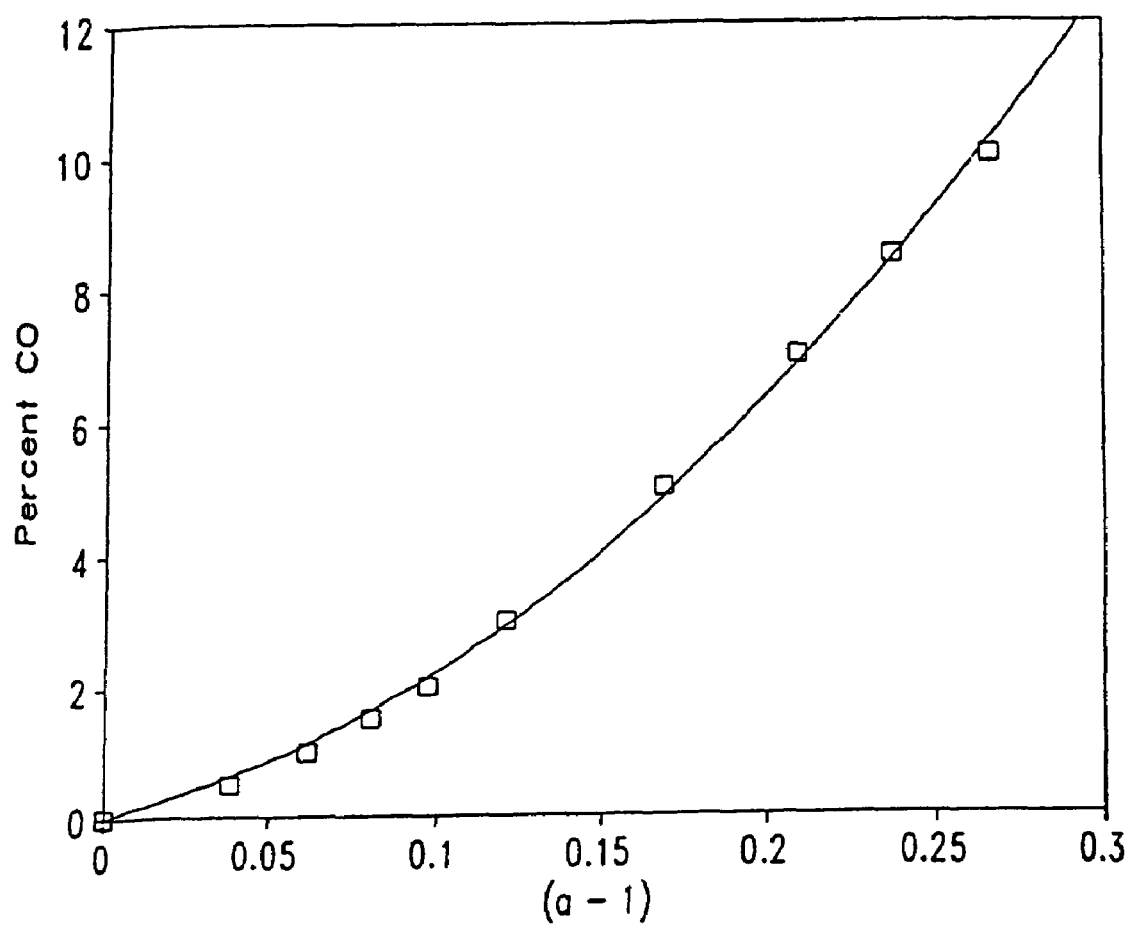
FIG. 3 illustrates a non-linear calibration curve for CO.

The HC gas cell calibration results in a linear correlation between absorption and HC concentration. FIG. 2, for example, depicts a calibration curve illustrating the linear calibration of an HC detector channel. The illustrated linear response provides the key to identifying the instantaneous CO and $CO_2$ column densities during a single gas pulse (or puff) calibration in a laboratory setting, as described in detail below. The use of single gas pulse calibration may assist in avoiding the effort previously expended to obtain the non-linear calibration curves for CO and $CO_2$. FIG. 3, for example, is an illustration of a non-linear calibration curve for CO. The illustrated curve was fit with a second order polynomial.

Figure 1B:
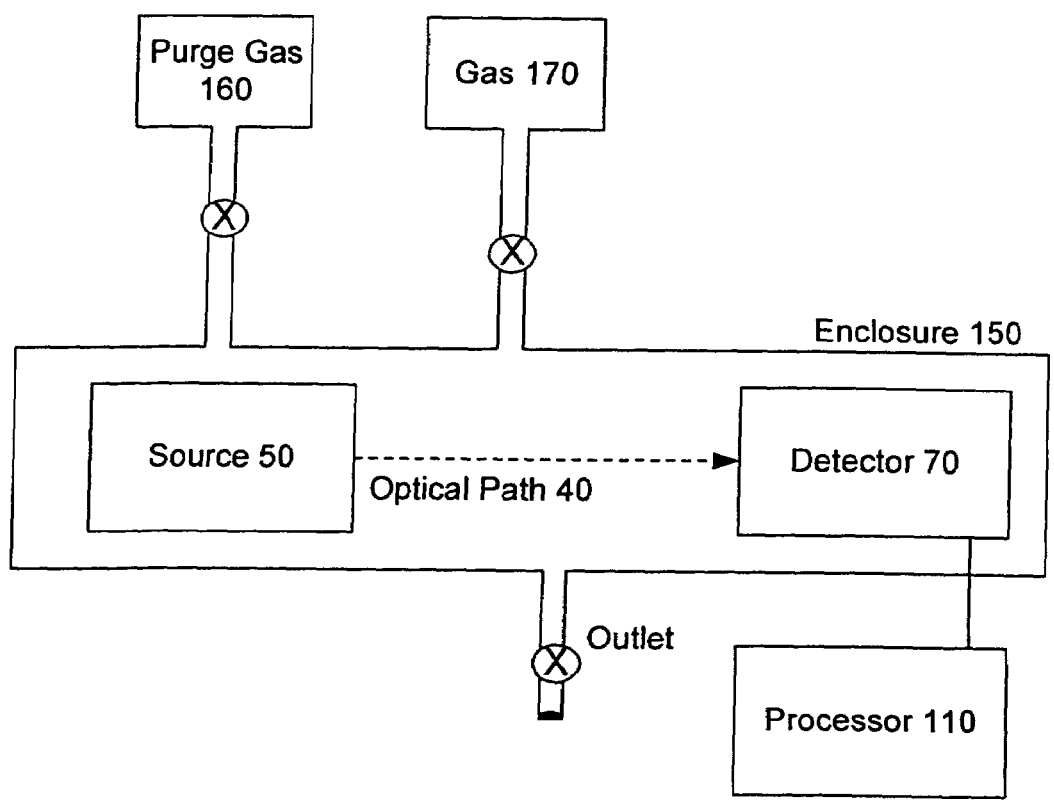
FIG. 1B is an exemplary illustration of an optical absorption-based multi-gas analyzer (OABMGA) placed under (or within) an enclosure in a laboratory environment, according to an embodiment of the invention.

In one embodiment, once the linear correlation between absorption and HC concentration has been obtained via HC gas cell calibration, source 50, detector 70, and optical path 40 may be isolated from outside (or ambient) air in the laboratory setting to accomplish single gas pulse (or puff) calibration. As illustrated in FIG. 1B, for instance, source 50 and detector 70 may be placed under (or within) enclosure 150. Enclosure 150 may comprise a plastic enclosure or other suitable covering device or mechanism for isolating source 50 and detector 70 from outside (or ambient air). In various implementations, processor 110 may be located either within or outside of enclosure 150.

According to an embodiment of the invention, prior to single pulse calibration, enclosure 150 may be purged with a gas from purge gas source 160 over a pre-determined period of time to purge out all of the CO, $CO_2$, HC, or other gases within optical path 40. In one implementation, the purge gas may comprise $N_2$, and enclosure 150 may be purged with $N_2$ during an overnight time period at a rate of approximately 1.0 L/min. Other time periods and purge rates may be utilized.

In one implementation, gas lines from gas source 170 (which may comprise a cylinder containing, for instance, a known gas mixture of CO, $CO_2$, HC, $N_2$, or other gases) may also be carefully purged with fresh gas not entering enclosure 150.

At the conclusion of the predetermined "purge" time period, source 50 and detector 70 may be powered on, and processor 110 may be configured to acquire raw voltage data from detector 70 for a predetermined acquisition duration. In one embodiment, the predetermined acquisition duration may comprise ten seconds. Once the predetermined acquisition duration has commenced, gas source (or cylinder) 170 may be opened (e.g., through the use of a solenoid or other valve) and a known gas mixture of CO, $CO_2$, HC, and $N_2$, or other gases may be passed into optical path 40 within enclosure 150. Any of the valves illustrated in FIG. 1B may be controlled manually, or in an automated manner via processor 110.

According to one embodiment of the invention, the gas mixture may be introduced into optical path 40 up to optical depths (the product of concentration times path length also termed column density) comparable to those seen on a roadway or other test surface in a real study (of vehicle emissions). This may be done such that the on-road data can be interpolated within the laboratory calibration rather than extrapolated outside the bounds of the calibration.

Figure 4:
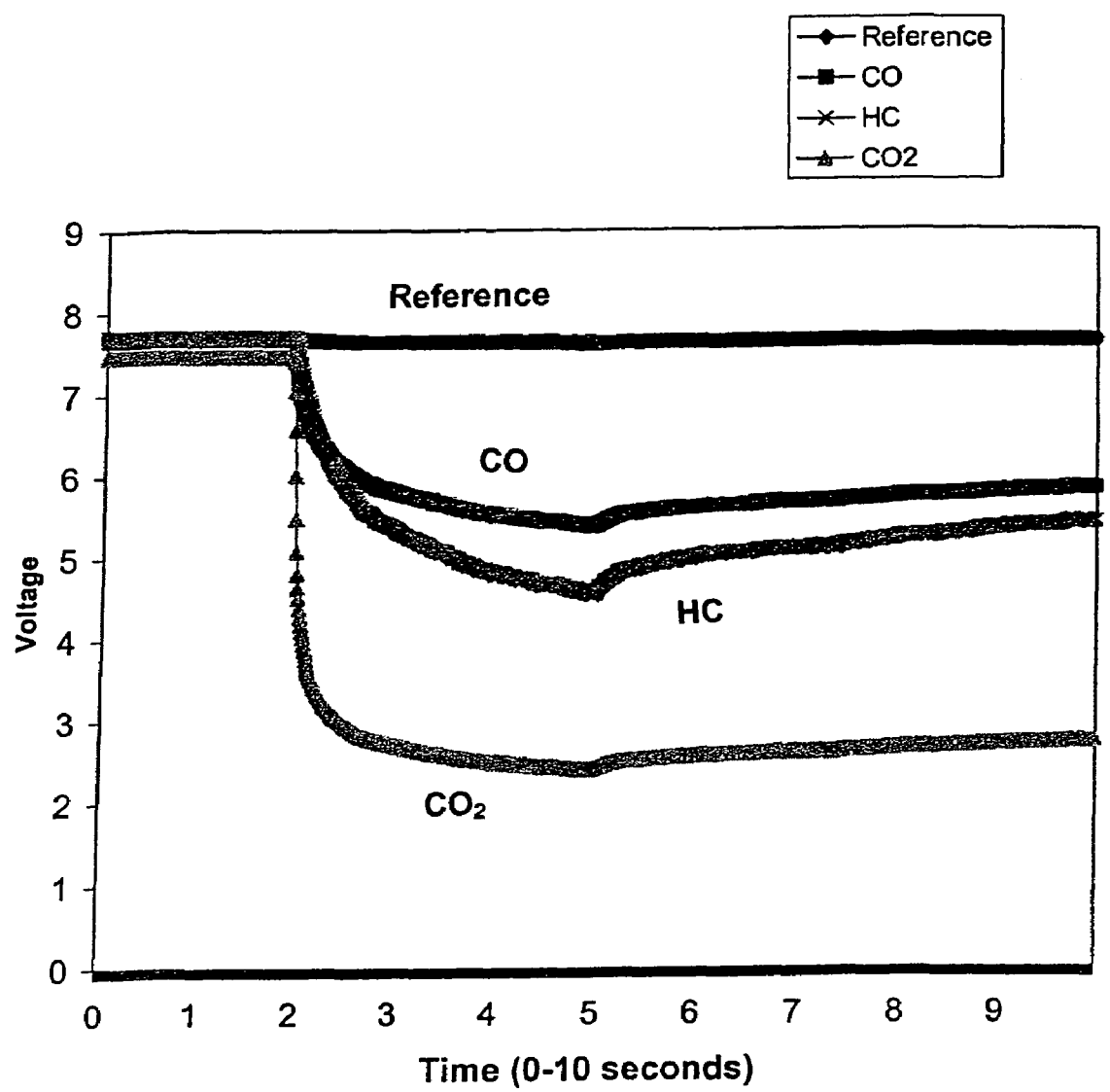
FIG. 4 illustrates raw voltages obtained using a calibration method, according to an embodiment of the invention.

FIG. 4 is an exemplary illustration of raw voltages obtained from a reference detector channel, in addition to CO, HC, and $CO_2$ detector channels over an acquisition duration of ten seconds. In this embodiment, voltage outputs were sampled every ten milliseconds for the ten second time period. Other sampling rates may be utilized. As shown, the gas mixture appears to have been introduced in a single puff into optical path 40 from approximately 1.7 seconds to 5. seconds during the total ten second time period.

Once data have been collected, processor 110 may process the data to produce a graph of absorbance vs. gas concentration in the following manner. In one implementation, all of the raw voltages may be ratioed to the reference voltage to negate any effect of electrical noise or source fluctuation using the following equation:

$$R_n = \frac{V_{Signal}}{V_{Reference}} \quad (1)$$

where $R_n$ is the reference ratioed signal voltage;

$V_{Signal}$ is the observed voltage on the detector channel of interest (CO, $CO_2$, or HC); and $V_{Reference}$ is the voltage on the reference channel.

In one implementation, all voltages may have subtracted a "dark" voltage obtained from the readings when the IR "zero" beam from source 50 is blocked. The cleanest air (e.g., the voltage readings at the beginning in FIG. 4 before the gas pulse (or puff) started), may be assumed to be when the gas concentration is equal to zero. Thus, these are referred to as the "$R_0$" values, or the reference ratioed voltages when the air is free of pollutant.

The absorbance of the system may be calculated using the equation:

$$A = \ln \frac{I_0}{I} \quad (2)$$

where A is absorbance;

$I_0$ is the light intensity absent pollutant; and

I is the measured light intensity when to pollutant is present.

In one embodiment, the absorbance data and concentration data may be established into a mathematical relationship to form a calibration equation. The concentration ratios $HC/CO_2$ and $HC/CO$ may be read from the gas source 170 (or cylinder), depicted in FIG. 1B, used for calibration. These ratios may be used for the calculation of real-time concentrations of CO and $CO_2$ gases because the previously performed HC calibration enables direct calculation of the instantaneous HC levels during the pulse (or puff).

Figure 5:
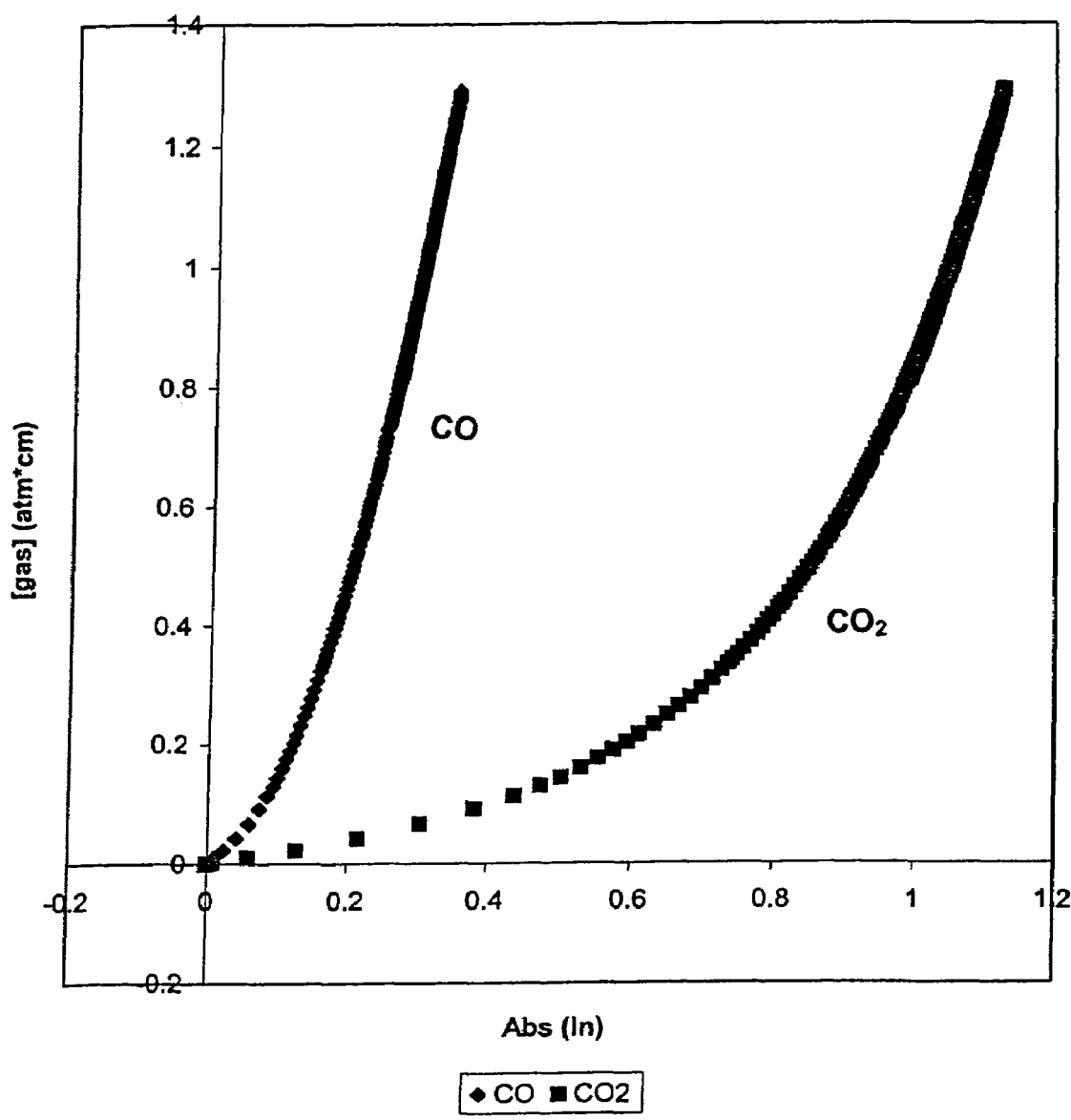
FIG. 5 illustrates calibration curves for CO and $CO_2$, according to an embodiment of the invention.

The HC calibration is the line whose slope is used to calculate the instantaneous HC concentration, and thus the $CO_2$ concentration and CO concentration values with the aid of the gas cylinder (or gas source 170) ratios. From the previous data, the calibration curves for $CO_2$ and CO may be obtained directly—calibrated using the known concentration values from the gas cylinder (or gas source 170). FIG. 5 is an exemplary illustration of calibration curves generated for $CO_2$ and CO.

According to an embodiment of the invention, with this graphical representation of the data (e.g., FIG. 5), a best-fit line may be applied to the data to mathematically relate the two axes and generate a calibration equation for CO and a calibration equation for $CO_2$. This fit may be carried out in at least two ways; the first is a second order polynomial fit (quadratic equation), and the other is an exponential growth curve (in the form of $y=a+e^{b+cx}$). Other arithmetic curve fitting equations may be used as known and understood by those having skill in the art.

When the laboratory calibration is completed, specific instrument software may be updated with the appropriate laboratory calibration equation for CO and the appropriate laboratory calibration equation for $CO_2$, and moved into a field measurement. The foregoing system and method, based on a single pulse (or puff) calibration, is less labor intensive than calibration performed one gas at a time.

Although the foregoing description was directed primarily to obtaining calibration curves for CO and $CO_2$, it should be recognized that the system and method described may be used to obtain calibration curves for other gases of interest in the same manner, thus avoiding the need to separately calibrate each detector channel with known column densities (optical depths) of relevant pollutant gases. As such, the foregoing description should not be viewed as limiting.

II. Exemplary Remote Emissions Sensing (RES) System

Figure 6:
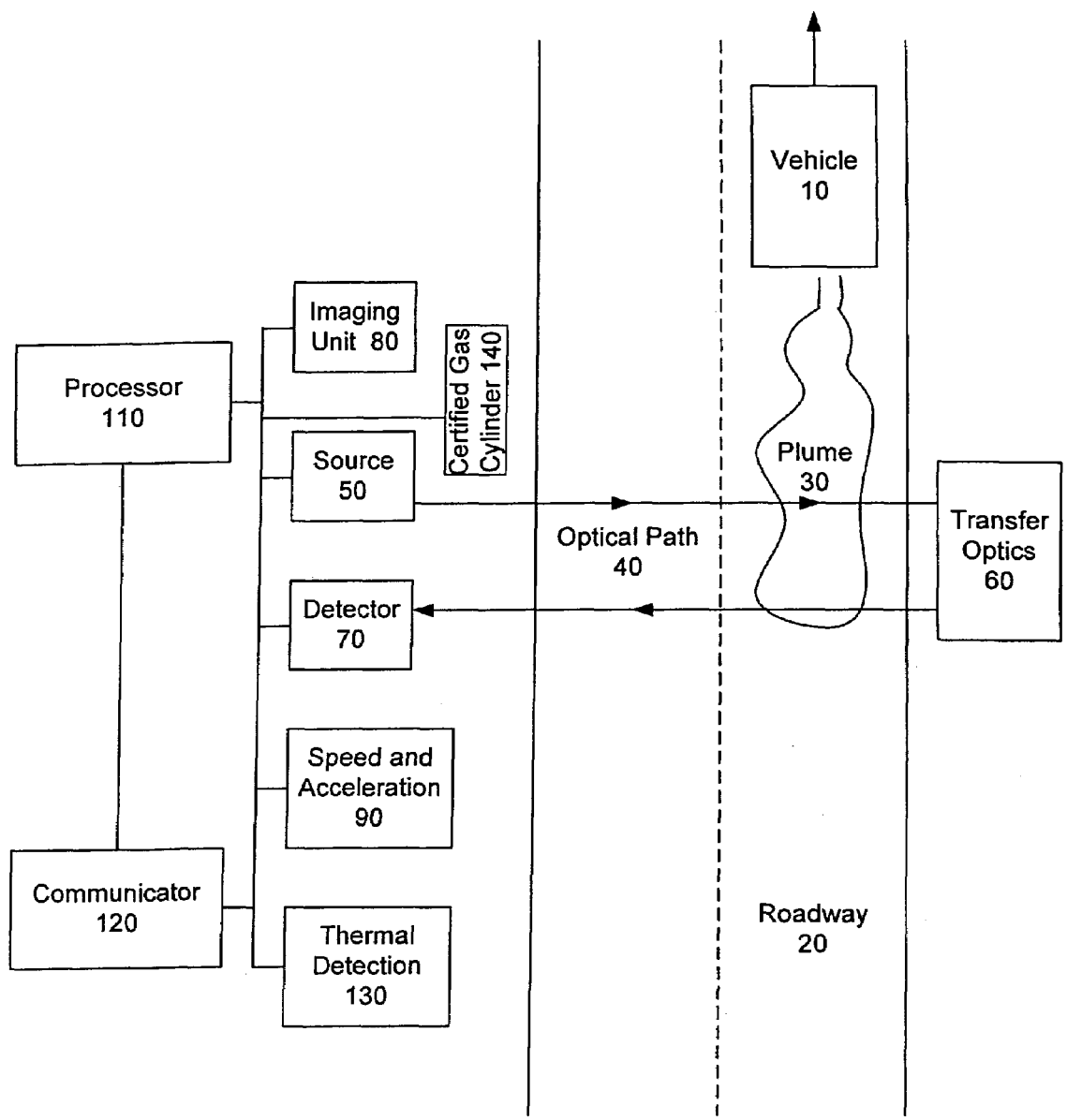
FIG. 6 is an exemplary illustration of a remote emissions sensing (RES) system, according to an embodiment of the invention.

Prior to setting forth a description of the self-calibration of on-road RES instruments to compensate for changes in background CO and $CO_2$ concentrations, a description of an exemplary RES system is provided with reference to FIG. 6. The calibration methods disclosed herein can be used with this or other system configurations. Embodiments of the invention may include some or all of the RES system components as described below, or other components.

According to one implementation, the RES system measures emissions in an exhaust plume 30 (from a motor vehicle 10) in an optical (or measurement) path 40 on a roadway 20. Roadway 20 may comprise a single or multi-lane roadway, or any other roadway or driving surface suitable for the safe passage of vehicle 10 under various operating conditions. Alternatively, roadway 20 may comprise a test lane designated for vehicle emissions testing, wherein vehicle 10 may be tested under a variety of operating conditions.

As previously recited, source 50 may comprise one or more sources of electromagnetic radiation (ER) and detector array 70 is preferably chosen to permit detection of electromagnetic radiation emitted by source 50.

According to one embodiment, the RES system may comprise transfer optics 60 mounted in a manner to allow radiation from source 50 to be reflected to detector array 70 for analysis. Transfer optics 60 may comprise a mirror, flat mirror, lateral transfer mirror (LTM), vertical transfer mirror (VIM), retroflector, or other device. In one embodiment, transfer optics 60 may comprise a lateral transfer mirror to reflect radiation from source 50 along a path displaced laterally or vertically, depending on orientation, from the incident direction. Other configurations may be used.

Processor 110, as described in detail above, may employ software to accomplish desired analysis of collected and/or stored data, and to carry-out one or more of the calculations described in the laboratory calibration methods and self-calibration methods set forth herein.

With regard to an exhaust gas sample present in optical path 40, software may be used to calculate the relative amounts of various exhaust gas constituents, concentrations of various exhaust gas constituents (e.g., HC, $CO_2$, $NO_x$, CO, etc.), the decay rate (e.g., dissipation in time) of the exhaust constituents, and the opacity of the exhaust plume.

According to an embodiment of the invention, processor 110 may calculate the relative amounts of various exhaust gas constituents in exhaust plume 30 of vehicle 10 (as vehicle 10 passes by (or through) the RES system) by computing the ratio of the absorption for a particular exhaust gas constituent to the $CO_2$ absorptions, in a known manner. This eliminates the need to calculate the total amount of exhaust plume present since the calculated ratios may provide sufficient information to identify vehicles which do not meet predetermined pollution criteria.

Processor 110 may also comprise software to accomplish other data analysis functions. For example, vehicle emission data may be checked for running losses. Running losses may typically include emission readings due to fuel system leaks on a vehicle (e.g., leaky fuel tank filler cap, fuel line, etc.), blow-by emissions (e.g., crank case emissions blowing by the piston rings), emissions due to other vehicles in the vicinity, or other systematic losses.

Processor 110 may also include software to accomplish various vehicle owner notification functions. For example, the owner of a vehicle that has been recorded as being in compliance with certain predetermined emission levels may receive a notification. Coordination with local authorities may be arranged to grant vehicle owners a waiver or pass of local emission certification procedures upon receiving such a notification. Likewise, vehicles that fail to meet predetermined emission levels may receive a notification requiring the owner to remedy the non-compliance. Other data processing functions are also possible. For example, processor 110 may control the release of gas from certified gas cylinder 140 for in-field calibration as described in greater detail below. Processor 110 may also interface to, control, and/or collect and reduce data from an imaging unit 80, a speed and acceleration detection unit 90, and thermal detection unit 130.

In various embodiments, the RES system may comprise an imaging unit 80 to capture and/or record an image of vehicle 10 passing by (or through) the RES system in a known manner. Imaging unit 80 may be positioned to record an image of vehicle 10 at any predetermined number of locations. Imaging unit 80 may comprise, for example, a film camera, video camera, or digital camera. Other imaging devices may also be used.

Preferably, imaging unit 80 may record an image of the identification tag (e.g., license plate) of vehicle 10. Tag information may be processed by processor 110 to provide additional information about the vehicle. For example, Motor Vehicle Department databases may be accessed to retrieve owner information, make, model type, model year, or other information. In some embodiments, this additional information may be incorporated into the emission sensing data analysis. For example, the make and model year of the vehicle may be used to determine input information for certain processing steps, including information such as whether the vehicle includes a carburetor or fuel injector, whether the car runs on diesel fuel or gasoline, etc.

According to an embodiment of the invention, the RES system may include a speed and acceleration detection unit 90. Preferably, the speed and/or acceleration of vehicle 10 may be measured as it passes through the RES system using speed and acceleration detection unit 90 in a known manner.

In one embodiment, speed and acceleration detection unit 90 may comprise an arrangement of laser beams or other light beams associated with timing circuitry. The laser or light beams may be arranged to traverse the path of vehicle 10 at various points. As vehicle 10 passes, it will cause interruptions in the laser or light beams. The times at which the beam interrupts occur may be used to calculate the vehicle's speed and/or acceleration. Other methods of determining vehicle speed and/or acceleration may also be used or incorporated into the RES system.

Alternatively, the laser or light beams may be arranged to traverse the path of vehicle 10 at a single point in the vehicle's path. For example, radar systems may be used to determine vehicle speed and acceleration. Alternatively, transducers, piezoelectric elements, or other "drive over" detectors may be placed at locations in the roadway to monitor vehicle passage. Preferably, speed and/or acceleration data may be input into processor 110 to help characterize vehicle operating conditions (e.g., accelerating or decelerating), or to determine which vehicle is to be associated with a particular sensor measurement. Other configurations and uses of speed and acceleration data are also possible.

Some embodiments of the invention may incorporate a thermal detection unit 130. Preferably, thermal detection unit 130 may comprise a non-contact thermometer system. For example, an IR thermometer may be used to optically detect the temperature of remote objects. Other temperature detection systems may also be used. Thermal detection unit 130 may, for example, be used to detect the temperature of portions of the vehicle passing through the RES system. Some embodiments may use direct sensing of the area of interest. For example, an IR thermometer may be aimed at the underside of a passing vehicle to detect the temperature(s) of vehicle components (e.g., engine, catalytic converter, muffler, etc.). Indirect sensing may also be used. For example, an IR thermometer may be aimed at the roadway to measure the heat of the passing vehicle which is reflected from the roadway surface.

Thermal information that is detected by thermal detection unit 130 may be used to indicate that an engine has just recently been started (e.g., the engine is "cold" or has not reached normal operating temperature). Such a cold engine reading may be used, for example, to initiate an alternative data processing routine. Certain embodiments of the invention may reduce the chance of a potentially misleading reading by also detecting the temperature of other portions of the vehicle. Other uses for collected thermal data are also possible. Thermal detection of the exhaust plume of a vehicle and/or ambient temperatures may also be used in connection with various aspects of the invention.

According to one embodiment of the invention, an identification tag on vehicle 10 may be read to identify the vehicle and associate particular sensed vehicle emission information with the vehicle. An identification tag, defined as a license plate above, may also comprise a transponder located on or within vehicle 10 (e.g., hung from a rear view mirror, placed on the dashboard, etc.), or that is integral within the vehicle (e.g., part of a global positioning system ("GPS"), located within the engine of the vehicle, or placed or mounted elsewhere). The transponder may transmit information about vehicle 10, including make and model of vehicle 10, engine characteristics, fuel type, the owner of vehicle 10, or other information which may be pertinent. According to an embodiment of the invention, a transponder may be used in connection with other functions. For instance, a transponder may also be used in connection with a toll pass, whereby a driver can electronically pay tolls via the transponder without stopping the vehicle.

An identification tag may also comprise a tag or decal that requires a reader. By way of example, an identification tag may comprise a decal with identifying marks (e.g., bar codes, infrared markings, etc.) containing information about vehicle 10. The decal may be located outside vehicle 10, such as on a front or rear bumper, on the under-side of vehicle 10, or any other location on vehicle 10 where the decal may be suitably read. A reader may observe the decal and thereby obtain information about vehicle 10. One embodiment employs a bar code placed on the roof of vehicle 10, which can be read by a reader placed above vehicle 10.

A receiver may be used to obtain information from an identification tag. According to an embodiment of the invention, an antenna may receive signals transmitted from an identification tag containing a transponder. Any type of conventional receiver may be used to receive signals. According to an embodiment of the invention, one reader and/or receiver may be used in connection with multiple lanes. Based on the signal received or the decal read, a receiver or reader may determine in which lane a particular vehicle is located at a particular time.

Processor 110 may receive information about vehicle 10 from a reader and/or receiver. According to an embodiment of the invention, processor 110 may receive vehicle information. Vehicle information and information obtained by sensing vehicle emissions may be stored. Processor 110 may correlate vehicle information received from an identification tag with the results from vehicle emissions sensing. Processor 110 may update a vehicle record to account for the results obtained by processing vehicle emission data, such as information regarding whether a vehicle has passed or failed predetermined emissions criteria.

According to an embodiment of the invention, the RES system may further comprise a communicator 120. Communicator 120 may communicate information such as, for example, measured vehicle emissions and identification tag information from the RES system to various other locations (e.g., Motor Vehicle Departments, a central data repository, servers, etc.) for storage, processing, viewing, or other use in a known manner. Communicator 120 may transmit and/or receive information via a wire connection, such as cable or telephone line, or a wireless connection, such as by a radio, cellular, or satellite transmitter, or via any other type of suitable wireless communication.

In some embodiments, communicator 120 may comprise appropriate hardware and/or software to enable processor 110 to be accessed remotely over a network (not illustrated) via a communications link (not illustrated). The network may include any one or more of, for instance, the Internet, an intranet, a PAN. (Personal Area Network), a LAN (Local Area Network), a WAN (Wide Area Network), a SAN (Storage Area Network), or a MAN (Metropolitan Area Network). The communications link may include any one or more of, for instance, a copper telephone line, a Digital Subscriber Line (DSL) connection, a Digital Data Service (DDS) connection, an Ethernet connection, an Integrated Services Digital Network (ISDN) line, an analog modem connection, a cable modem connection, or a wireless connection. In this regard, a user (e.g., an emissions test administrator or other individual) at a remote computer terminal can administer emissions tests, and/or analyze or process data. Thus, the RES system may, in various embodiments, comprise either manned or unmanned systems.

As recited above, alternative RES system configurations may exist incorporating some or all of the aforementioned system components. Accordingly, the RES system illustrated in FIG. 6 should not be viewed as limiting.

As an example, in certain embodiments (not illustrated), source 50 and detector 70 may be placed on opposite sides of roadway 20. Various components of speed and acceleration detection unit 90 and thermal detection unit 130 may also be positioned on opposite sides of roadway 20.

In another embodiment (not illustrated), the RES system may comprise a compact, unmanned system that may be used for unattended monitoring of vehicle emissions data (also referred to as a "bunkered" unit). In such an embodiment, source 50, detector 70, imaging unit 80, processor 110, communicator 120, and various components of speed and acceleration detection unit 90 and thermal detection unit 130 may be housed together on a first side of roadway 20, while transfer optics 60 and various other components of speed and acceleration detection unit 90 and thermal detection unit 130 may be housed together on the opposite side of roadway 20. Other configurations are possible. Emissions and other measured data may be transmitted by communicator 120 as described in detail above.

III. Self-Calibration

In certain instances, when remotely monitoring the exhaust gas composition of motor vehicles on a roadway or driving surface under various operating conditions using a RES system similar to that described in FIG. 6, it may be expensive and/or inconvenient to have to repeatedly recalibrate on-road RES instruments using expensive certified gas cylinders of surrogate exhaust pollutants.

Such recalibration may be required for conventional instruments because the same measured voltage change (even when converted to absorbance) on the $CO_2$ and CO channels can correspond to a different amount of gas at different times of the day because the absorbance versus column density graph is non-linear (e.g., the Lambert-Beer absorption law does not hold). Stated in another way, one problem is that, where signals fall on the absorption curves referenced above, depends upon the background concentrations of the relevant pollutant. $CO_2$ in particular is reasonably abundant in the atmospheric optical path used for measurement, and may vary with wind speed, wind direction, and traffic volume, among other factors.

According to an embodiment of the invention, to be "self-calibrating," RES instruments may be adapted to continuously monitor the changes in background (or ambient) concentrations of those pollutants which have non-linear, background-dependent calibration curves, so as to remain correctly calibrated.

In particular, a combination of signals from detector channels which respond to the pollutants in question, and detector channels which provide reference signals, may be utilized. The detector channels may be provided by either a plurality of detectors with different optical filters, or a single detector observing through a plurality of optical filters. In one implementation, the optical filters may include gas cells as in the method known as gas filter correlation spectroscopy. In one embodiment, a first detector channel may monitor $CO_2$ at an IR wavelength of approximately 4.3 micron absorption, and a reference channel may monitor an IR wavelength of approximately 3.9 microns at which no gas absorption is expected. With this capability, a RES instrument may be calibrated once in the laboratory (as described above), and then used to obtain correct readings at virtually any location in the field without recalibration.

According to one implementation, local background pollutant concentrations at a vehicle emissions test site may be determined using a gas puff from cylinder 140, or the insertion of a gas cell with known pollutant concentrations. In this regard, any individual channel gain changes which might have taken place since the laboratory calibration may be accounted (or corrected) for. Background levels may be continuously updated based upon voltage signals collected in front of passing motor vehicles whose emissions are to be quantitatively detected. Pollutant background changes as a function of time may be evaluated to identify both slow and fast changes, and the software accepting vehicle emissions readings may be adjusted depending upon how stable the background concentrations are measured to be.

According to an embodiment of the invention, detector array 70 may be configured such that each gas (or constituent) of exhaust plume 30 has a unique detector channel. For a gas of interest, a band-pass filter may be configured to pass radiation having a particular wavelength or range of wavelengths to a detector. The particular wavelength or range of wavelengths may be selected to correspond to wavelengths absorbed by the gas of interest. For a given band-pass filter channel for one gas, there is one absolute calibration curve of absorption vs. gas column density (e.g., similar to that shown in FIG. 5 for both CO and $CO_2$). In a laboratory setting, the filter may be calibrated all the way from no gas in the optical path, up to a practical limit of feasible gas column density that may be present on the road.

Currently, in the field, a single gas puff calibration may be used to determine the background concentration of $CO_2$ and the theoretical "$R_0$" value. As recited above, the $R_0$ value may comprise the reference ratioed voltage when the air is free of pollutant. Although not illustrated, a gas cell with a known admixture of pollutants may also be used for this application. Although an $R_0$ value was calculated in the laboratory calibration, the $CO_2$ voltage to Reference voltage ratio may change irrespective of one another if gain potentiometers are changed in the circuitry of the instrument, or if other changes to the hardware are made. Accordingly, it is sometimes appropriate that the new $R_0$ be calculated in the field. This recalibration may negate any of the aforementioned changes (or other changes) from adversely affecting the absolute calibration, and may enable freedom of hardware modifications without need for redoing the laboratory calibration.

In one implementation, to perform this single field calibration, a half-second (or other duration) gas puff from certified gas cylinder 140 may be made in optical path 40 (in the field) and, using known, absolute calibration curves, processor 110 may calculate what the $R_0$ and $CO_2$ background "$CO_2B$" is at the test site (in the field). Certified gas cylinder 140 may contain, for example, a known mixture of CO, $CO_2$, and HC (similar to the lab calibration described above). The calculation procedure, according to one embodiment, is set forth below.

According to an embodiment of the invention, a preliminary assumption is that all column densities (in the case of a half-second there may be for instance fifty readings, one for each 10 ms averaging period) calculated are assumed to be in an 8 cm. cell, although the actual path length may be much larger.

All voltages may first be normalized to reference, providing $R_n$s for all channels and readings, where $R_n$s is (Vsignal-Vdark)/(Vref-Vdark) for each time (n) and substance/pollutant(s) [see equation 1]. Vdark readings may be measured either when the optical beam is blocked by a vehicle, or at the beginning of the day when blocked by an operator.

Next, the "clean air" or air with the smallest absorptions apparent in the puff may be located in time. This time may comprise the time of the highest $CO_2$ voltage of the fifty readings (least absorption). These "smallest" ratios may be termed $R_{HClow}$, $R_{COlow}$, and $R_{CO2low}$. The time of these may be defined as $T_{min}$.

The lowest HC voltage of the fifty readings may then be identified, which corresponds to the highest HC column density, and is termed $R_{HChi}$. $R_{HChi}$, together with $R_{COhi}$ and $R_{CO2hi}$ may all be set at that same point in time, $T_{max}$.

$\Delta HC$ may then be calculated using the following equation:

$$\Delta HC = \frac{H_1(R_{HClow} - R_{HChi})}{R_{HChi}} \qquad (3)$$

wherein $\Delta HC$ is the apparent change in HC column density;

$H_1$ is the laboratory slope for the linear HC calibration (e.g., FIG. 2); and $R_{HClow}$ and $R_{HChi}$ are as defined above.

This calculation may be performed for every point along the puff data where $R_n \neq R_0$, and wherein $R_n$ is as defined above ($R_n$s).

Next, using the ratios of CO/HC and $CO_2$/HC from certified gas cylinder 140 used during the field calibration, the "true" column densities of CO and $CO_2$ in optical path 40 at the time of field calibration may be calculated. This can be achieved because from the $\Delta HC$ data and the cylinder ratios, the $\Delta CO$ and $\Delta CO_2$ may be calculated at each of the fifty time points during the calibration puff.

Overall, the $\Delta CO_2$ is equal to the $CO_2$ column density at $T_{max}$ minus the $CO_2$ column density at $T_{min}$:

$$\Delta CO_2 = CO_{2Max} - CO_{2Min} \qquad (4)$$

wherein $CO_{2Max}$ is the $CO_2$ column density at $T_{max}$; and $CO_{2Min}$ is the $CO_2$ column density at $T_{min}$.

Knowing that there was background $CO_2$ or "$CO_2B$" even at what is assumed to be the "clean air" column density at $T_{min}$, it is assumed that $CO_2B$ is equal to the $CO_2$ column density at $T_{min}$:

$$CO_2B = CO_{2Min} \qquad (5)$$

The field puff has given a known $\Delta CO_2$ and an apparent absorbance for each of the 50 points during the half-second puff. Processor 110 may then determine at which location along the absolute laboratory calibration curve the instrument is currently operating. In the case where the absolute calibration equation is quadratic in form, the following algebra may be used:

$$CO_{2Max} = C_1 abs_{hi} + C_2 abs_{hi}^2 \qquad (6)$$

$$CO_2B = C_1 abs_{lo} + C_2 abs_{lo}^2 \qquad (7)$$

$$CO_2B + \Delta CO_2 = C_1\left(\frac{R_0}{R_{hi}} - 1\right) + C_2\left(\frac{R_0}{R_{hi}} - 1\right)^2 \qquad (8)$$

The terms $C_1$ and $C_2$ are coefficients derived from the laboratory calibration. It should also be recognized that A* has been replaced above with "abs" (standing for absorbance). These absorbance numbers are a function of the known $R_n$ values in the calibration and the unknown, but calculable $R_0$.

In equations (6)-(8):

$abs_{hi}$ is $(R_0/R_{hi}-1)$;

$abs_{lo}$ is $(R_0/R_{lo}-1)$; and $R_{hi}$ is as defined above.

The above derivation results in two simultaneous equations with two unknowns ($R_0$ and $CO_2B$). They are solved for both variables. Algebraic derivation yields a quadratic solution:

$$R_0 = -b \pm \sqrt{\frac{b^2 - 4ac}{2a}} \qquad (9)$$

Where:

$$a = C_2\left(\frac{R_{lo}}{R_{hi}} - \frac{R_{hi}}{R_{lo}}\right) \qquad (10)$$

$$b = (C_1 - 2C_2)\frac{R_{lo}}{R_{hi}} \qquad (11)$$

$$c = -R_{lo}R_{hi}\Delta CO_2 \qquad (12)$$

In equations (10)-(12), $R_{lo}$ is as defined for $R_{low}$ above.

The numerical solution for $R_0$ (the theoretical $CO_2$ to reference voltage ratio that would have been observed had the $CO_2$ column density equaled zero) may be used to solve for $CO_2B$ at the time of field calibration. The solution becomes:

$$CO_2B = C_1\left(\frac{R_0 - R_{lo}}{R_{lo}}\right) + C_2\left(\frac{R_0 - R_{lo}}{R_{lo}}\right)^2 \qquad (13)$$

The $CO_2B$ and $R_0$ values may be stored in a data file or database (not illustrated) operatively connected to processor 110. $R_0$ is used and $CO_2B$ is updated until the instrument is recalibrated, which may occur, for instance, when it is next setup at another site.

According to an embodiment of the invention, the "cleanest air" $CO_2$ to reference voltage ratio is used to determine a specific $CO_2B$ for each reading of a vehicle's exhaust emissions. Thus, $CO_2B$ can change as each car passes. This allows for a quadratic or other non-linear equation to be used to correct for $CO_2$ for each passing vehicle. This remains an empirical method. The absorption vs. column density data may be manipulated in any mathematically equation to conveniently relate the two. A quadratic equation may not always be a good fit to the empirical data. An exponential growth curve, for instance, may turn out to be a better fit.

Figure 7:
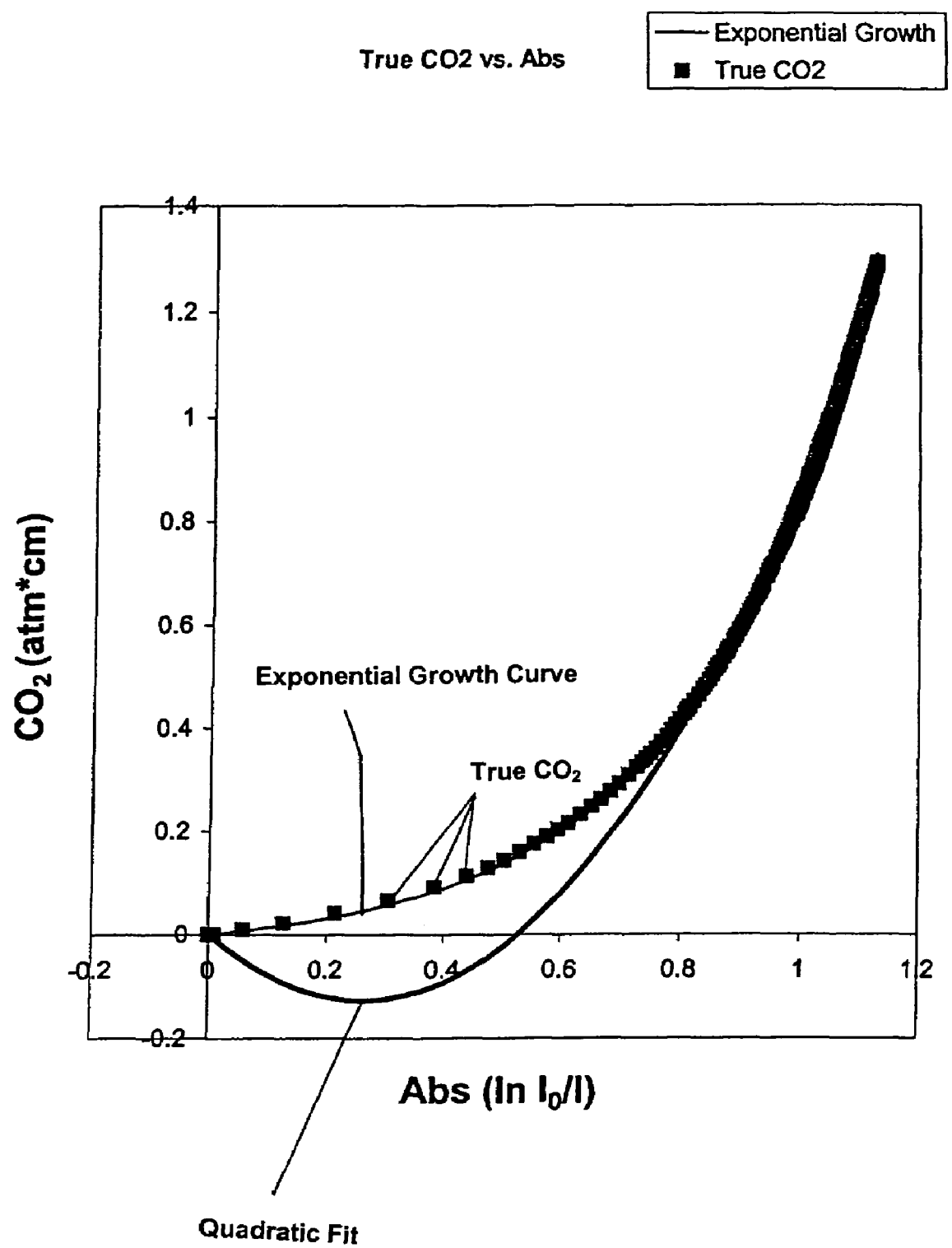
FIG. 7 illustrates a calibration curve, according to an embodiment of the invention.

FIG. 7 illustrates a calibration curve wherein the exponential growth curve used as the empirical fit is almost indistinguishable from the calibration data, whereas the quadratic fit of the data grossly underestimates the column density of $CO_2$ near x=0. The poor quadratic fit may arise partly because most of the 1000 data points are above a column density of 0.4 atm*cm of $CO_2$.

According to an embodiment of the invention, an exponential growth curve can be fit with the change of absorbance and the concentration input from certified gas cylinder 140, and iteratively solved for a $CO_2B$ and an $R_0$ in the field much more quickly and effectively than with closed form solutions. As such, processor 110 may be input with the laboratory-calculated curves, and may iteratively fit the field calibration data to solve for the $CO_2B$ and an $R_0$.

The treatment of the data is quite similar in both quadratic and exponential methods, in that the zero-corrected voltage data may all be reference ratioed to acquire $R_n$ values. From these Rn values, the "cleanest" and "dirtiest" air data points may be found and set as the respective $R_{lo}$ and $R_{hi}$ values. Natural log $(R_{lo}/R_n)$ may then be calculated as the absorbance value to be used in calibration. The HC data may be used, and calculated back against the laboratory line. $\Delta HC$ may be calculated at each point, thus giving the amount of HC added during the calibration puff. Using the cylinder ratios of $HC/CO_2$ and $HC/CO$, the $\Delta CO_2$ and $\Delta CO$ may be calculated as well.

In the first iteration to be tested, it may be assumed that $R_{lo}=R_0$ for the instrument. Using the exponential growth curve from the laboratory and the known $R_{hi}$ & $R_{lo}$ (assumed temporarily to be $R_0$), the first approximation of $\Delta CO_2$ may be calculated using the equation:

$$[CO_2] = a + e^{b+c\left(\ln\frac{R_{lo}}{R_{hi}}\right)} \quad (14)$$

where $[CO_2]$ is the $CO_2$ column density. Since the assumed $CO_2B$ is zero, $CO_{2hi}-\Delta CO_2-CO_2B<0$. If that answer comes out, as expected, to be negative, the iteration is continued, and a new iteration may be started at a point $CO_2B=CO_2B_{previous}+0.0064$ atm*cm. Using this new $CO_2B$, the inverse calibration equation is solved:

$$\ln\left(\frac{R_{lo}}{R_0}\right) = \frac{\ln([CO_2]-a)-b}{c} \quad (15)$$

A new $R_0$ is thus determined. Using this $R_0$, $R_{lo}$, and $R_{hi}$, the $\Delta CO_2$ can be calculated. Again, if $CO_{2hi}-CO_2B-CO_{2added}<0$, the iteration is continued, and a new one begins once 0.0064 atm*cm is added to the initial $CO_2B$.

This iteration may be continued until $CO_{2hi}-CO_2B-CO_{2added}\geq 0$. At this point, the iteration may be stopped and the $R_0$ used for that iteration is logged into a computer calibration file, as it is the accepted value for the $R_0$. Once the proper $R_0$ is calculated, an on-screen display may illustrate the full curve of $[CO_2]_{calculated}$ vs. $[CO_2]_{input}$. Since the instrument calculates the column density of $CO_2$ based on the calculated $R_0$, the "calculated" side represents the instrument's analysis of what is in the cylinder. The "input" axis may be obtained using the HC and the known cylinder ratios to determine how much $CO_2$ was actually put into the instrument. Therefore, the graphs (both for $CO_2$ and CO) should be linear with a slope of one.

Figure 8:
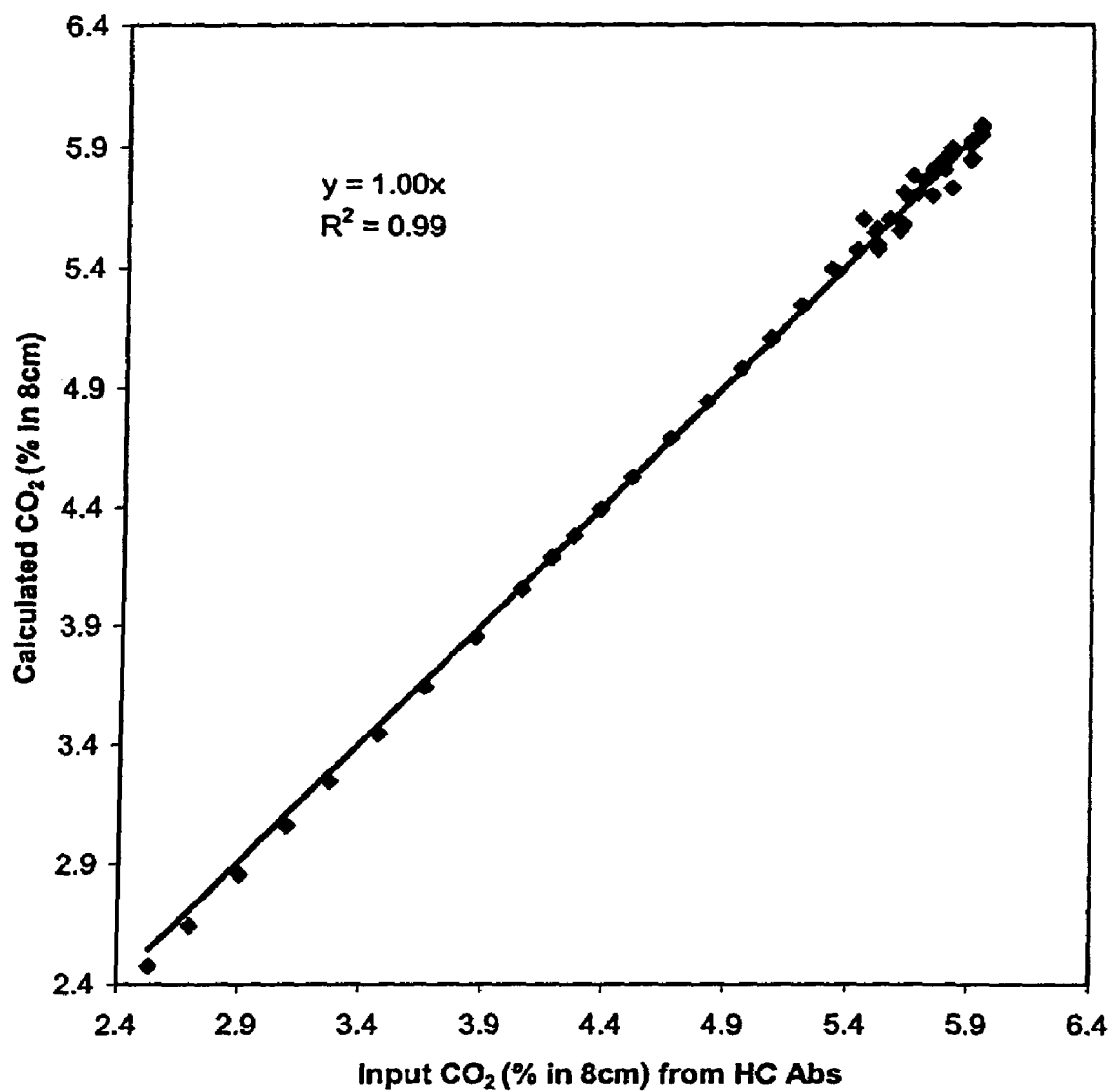
FIG. 8 illustrates a correlation graph, according to an embodiment of the invention.

FIG. 8 is an exemplary illustration of a correlation graph that may appear on-screen during a successful on-road gas puff calibration. If such a graph does not appear linear, with a slope of one, an operator may be alerted that there is a problem to be fixed. The operator may accordingly fix and recalibrate the instrument before measurements are taken. Once this field calibration is accepted and data are taken, for each vehicle reading, a new $CO_2B$ is calculated from the $CO_2$ to Reference voltage ratio. In this regard, processor 110 may properly use the absorption data to derive the $\Delta CO_2$ for the exhaust plume seen. A similar process may be used for CO.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A method of generating calibration curves for implementation in an optical absorption-based multi-gas analyzer (OABMGA), comprising:
    injecting, into an optical path between an electromagnetic radiation source and a detector, a time-variable puff of gas from a container, wherein the container comprises a mixture of gases at known concentration ratios, and wherein the mixture of gases includes a first gas and other gases;
    determining a concentration of the first gas in the puff of gas in the optical path based on a measured absorption of electromagnetic radiation, from the electromagnetic radiation source, due to the presence of the first gas in the optical path and a predetermined calibration curve for the first gas;
    determining a concentration of one or more of the other gases in the optical path based on the determined concentration of the first gas in the optical path and the known concentration ratios for the mixture of gases; and
    generating calibration curves for one or more of the other gases based on the determined concentrations of the one or more other gases.

2. The method of claim 1, wherein the first gas comprises propane, which is used as a surrogate hydrocarbon.

3. The method of claim 1, wherein the predetermined calibration curve for the first gas is obtained by inserting, into the optical path, a gas cell having a known concentration of the first gas.

4. The method of claim 1, wherein the other gases in the mixture of gases include at least CO and $CO_2$.

5. The method of claim 1, wherein the electromagnetic radiation source, detector, and the optical path there-between are isolated from ambient air via an enclosure, and wherein the time-variable puff of gas is injected into the optical path within the enclosure.

6. The method of claim 5, wherein the enclosure is first purged with a purge gas for a pre-determined time period to purge any gases present within the optical path prior to injecting the time-variable puff of gas into the optical path.

7. The method of claim 6, wherein the purge gas comprises $N_2$.

8. A system for generating calibration curves for implementation in an optical absorption-based multi-gas analyzer (OABMGA), comprising:

an optical path extending between an electromagnetic radiation source and a detector;

a container that injects a time-variable puff of gas into the optical path, wherein the container comprises a mixture of gases at known concentration ratios, and wherein the mixture of gases includes a first gas and other gases; and a processor that is configured to:

determine a concentration of the first gas in the puff of gas in the optical path based on a measured absorption of electromagnetic radiation, from the electromagnetic radiation source, due to the presence of the first gas in the optical path and a predetermined calibration curve for the first gas;

determine a concentration of one or more of the other gases in the optical path based on the determined concentration of the first gas in the optical path and the known concentration ratios for the mixture of gases; and generate calibration curves for one or more of the other gases based on the determined concentrations of the one or more other gases.

9. The system of claim 8, wherein the first gas comprises propane, which is used as a surrogate hydrocarbon.

10. The system of claim 8, wherein the predetermined calibration curve for the first gas is obtained by inserting, into the optical path, a gas cell having a known concentration of the first gas.

11. The system of claim 8, wherein the other gases in the mixture of gases include at least CO and $CO_2$.

12. The system of claim 8, wherein the electromagnetic radiation source, detector, and the optical path there-between are isolated from ambient air via an enclosure, and wherein the time-variable puff of gas is injected into the optical path within the enclosure.

13. The system of claim 12, wherein the enclosure is first purged with a purge gas for a pre-determined time period to purge any gases present within the optical path prior to injecting the time-variable puff of gas into the optical path.

14. The system of claim 13, wherein the purge gas comprises $N_2$.

* * * * *